United States Patent [19]

Steele et al.

[11] Patent Number: 4,734,988

[45] Date of Patent: Apr. 5, 1988

[54] METHOD OF ALIGNING A COLLIMATOR TO A LINEAR ARRAY X-RAY DETECTOR

[75] Inventors: Douglas S. Steele, Fairfield, Ohio; Casmir R. Trzaskos, Amsterdam, N.Y.

[73] Assignee: General Electric Company, Cincinnati, Ohio

[21] Appl. No.: 832,981

[22] Filed: Feb. 25, 1986

[51] Int. Cl.⁴ .............................................. G01B 5/25
[52] U.S. Cl. ..................................... 33/645; 33/181 R; 33/520
[58] Field of Search ............. 33/180 R, 181 R, 185 R, 33/286, 520

[56] References Cited

U.S. PATENT DOCUMENTS

| | | | |
|---|---|---|---|
| 3,289,298 | 12/1966 | Standridge | 33/286 |
| 4,356,223 | 10/1982 | Iida et al. | 33/180 R |
| 4,414,749 | 11/1983 | Johannsmeier | 33/180 R |
| 4,563,820 | 1/1986 | Isohata | 33/180 R |
| 4,570,343 | 2/1986 | Bell | 33/180 R |
| 4,601,560 | 7/1986 | Isohata et al. | 33/180 R |

Primary Examiner—Willis Little
Attorney, Agent, or Firm—Derek P. Lawrence

[57] ABSTRACT

A method for aligning a X-ray beam collimator to a linear array X-ray detector. The method computes a horizontal centerline on the detector and a horizontal centerline the collimator. The horizontal centerlines are then aligned. Vertical centerlines are computed for the detector and collimator. A thickness for a shim is computed from the difference in the vertical centerlines. The collimator is installed on vertical standoffs with the shims inserted between the collimator and standoffs. The shims align the collimator and detector in the vertical direction.

3 Claims, 2 Drawing Sheets

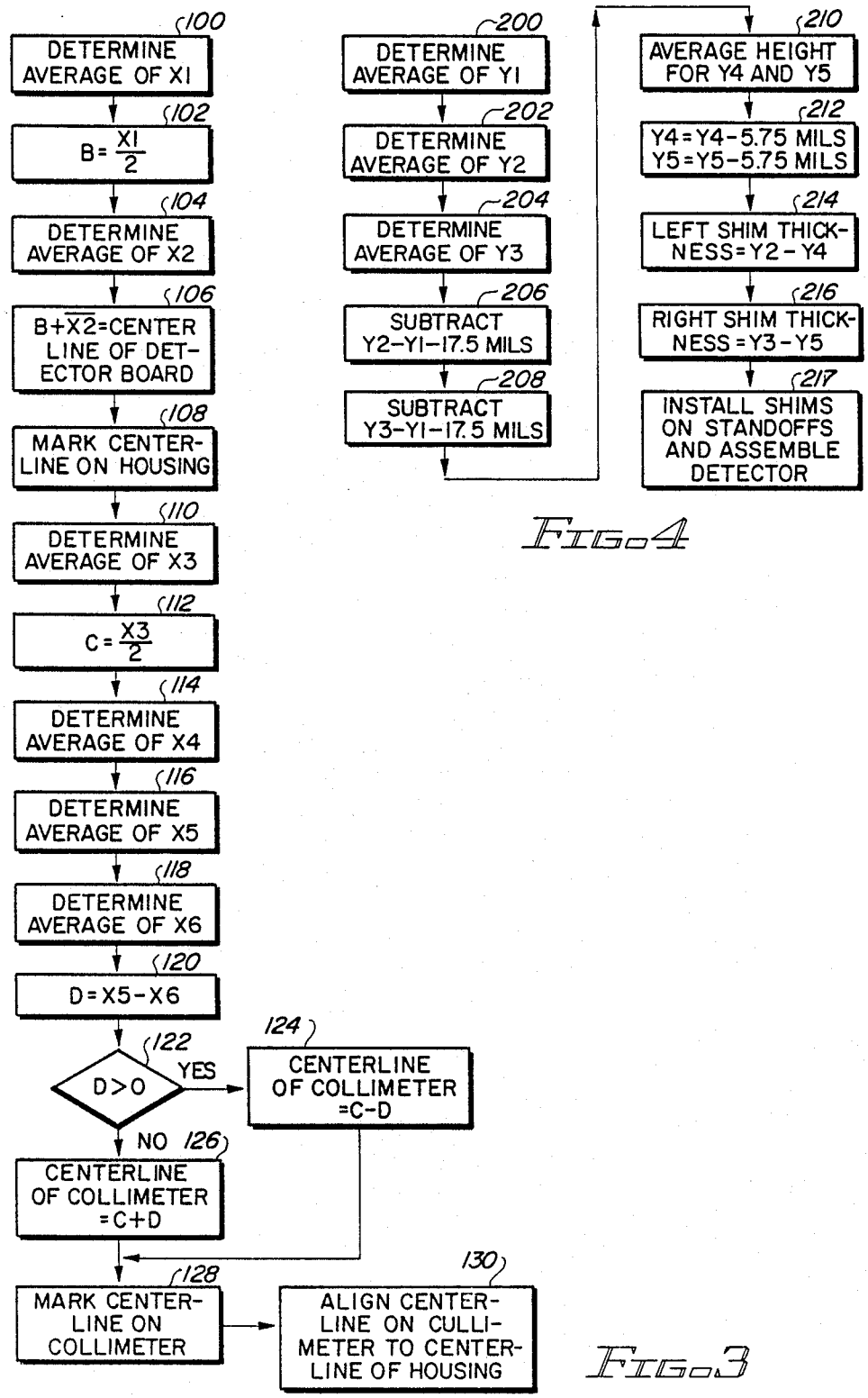

METHOD OF ALIGNING A COLLIMATOR TO A LINEAR ARRAY X-RAY DETECTOR

BACKGROUND OF THE INVENTION

A. Field of the Invention

This invention generally relates to a method of assembling X-ray detectors, and more particularly, to a method of aligning an X-ray beam collimator to a linear array X-ray detector

B. Background Discussion

An X-ray inspection system is comprised of hardware for manipulating parts, generating X-rays and detecting X-rays, hardware for information transmission and computation, software for controlling the X-ray image system and performing computations. Parts are carried into an X-ray machine by a multistation conveyor. An operator loads parts onto the conveyor which are held to the conveyor by a gripper. When the conveyor advances to an inspection station, a numerically controlled part manipulator grasps the gripper and part and moves the part into the X-ray beam. Moving the part vertically through the X-ray beam, a linear array X-ray detector measures the intensity of the X-ray beam for producing a digital fluoroscopy image of the part. A computed tomography image is taken of the part by rotating the part 360 degrees about the vertical axis. After collecting the data, the part manipulator moves the part and gripper to the conveyor belt where the computer system moves the gripper and part to an unload station.

The detector is a linear array detector having individual detector elements in a linear array across the face of the detector. A collimator across the front of the detector prevents scattered radiation from reaching the detector elements. To obtain a maximum signal on all the detector elements, it is necessary to align the center of the collimator vertically and horizontally to the center of the linear array detector.

Therefore, it is an object of this invention to provide a method for aligning an X-ray detector collimator to a linear array X-ray detector for producing a maximum signal on all detector elements.

It is a further object of the invention to provide a method for aligning the center of the X-ray beam collimator to the center detector element of the linear detector array.

It is a further object of this invention to provide a unified assembly for X-ray beam collimator and linear array detector for preventing movement of the collimator with respect to the linear detector array.

SUMMARY OF THE INVENTION

The X-ray detector includes an X-ray detector board, a base plate, a rear flange, a xenon gas housing, a collimator and standoffs. The method begins by computing an average for the horizontal width of the detector board in the housing, measuring the average distance from the right edge of the rear flange to the detector board, and computing a horizontal centerlilne of the detector and marking it on the detector assembly. Next the centerline for the horizontal collimator is computed and the centerline marked on the horizontal collimator. Next the vertical height of the detector board on each side is determined. The vertical height of the collimator standoffs are determined. If the standoffs do not support the collimator at the appropriate vertical height, calibrated shims are inserted between the standoff and the collimator for aligning the vertical center of the collimator with the vertical centerline of the detection assembly. The collimator is then attached to the standoffs with the calibrated shims, while aligning the horizontal centerlines of the collimator and detector.

BRIEF DESCRIPTION OF THE DRAWINGS

FIG. 3 is a flow diagram of a method for computing the horizontal centerline of the collimator and detector board.

FIG. 4 is a flow diagram of a method for computing the thickness of the calibrated shims.

DETAILED DESCRIPTION OF THE INVENTION

Figure 1:
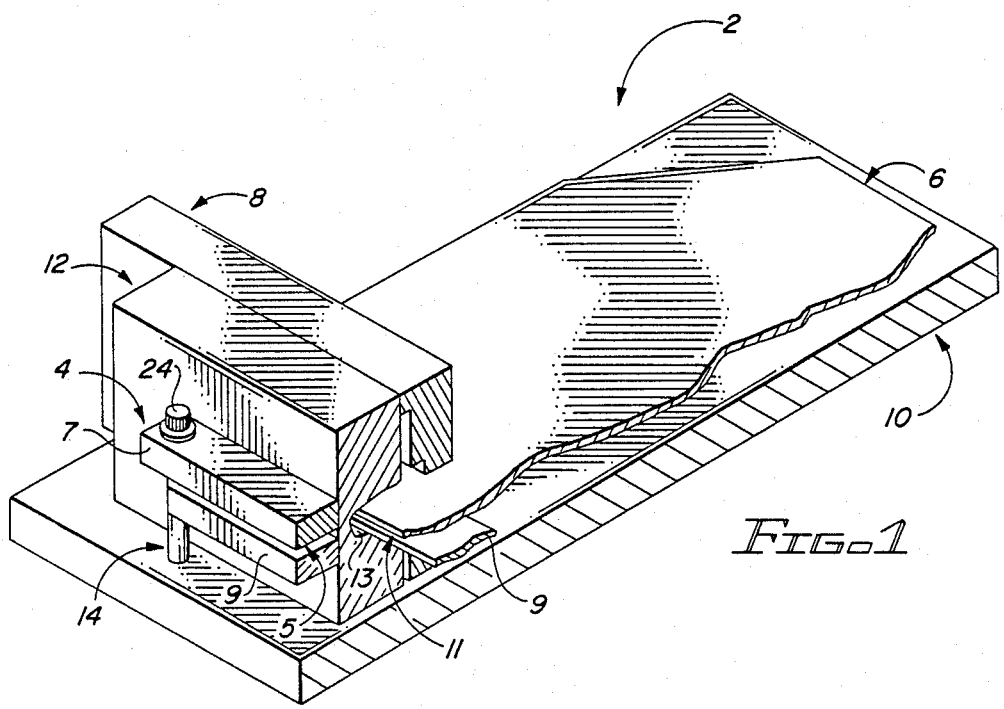
FIG. 1 illustrates a cut-away view of the detector assembly and collimator.

Referring to FIG. 1, in an X-ray inspection system a linear array detector assembly 2 measures the intensity of an X-ray beam generated from an X-ray source (not shown). For a more detailed description of the X-ray inspection system reference is made to U.S. patent application Ser. No. 832,511, titled X-ray Inspection System, filed concurrently herewith, assigned to General Electric Company, the disclosure of which is hereby incorporated by reference. A collimator 4 prevents scattered radiation from impinging on the linear array detector board 6. The collimator enables substantially parallel X-rays to travel as a thin sheet to strike the gas below the linear array detector board. The X-rays ionize the gas and the ions, under a high voltage potential migrate towards and are captured by elongated detector elements 11 beneath detector board 6. To produce a maximum signal on each detector element the collimator 4 is aligned vertically and horizontally with the detector board 6.

Figure 2:
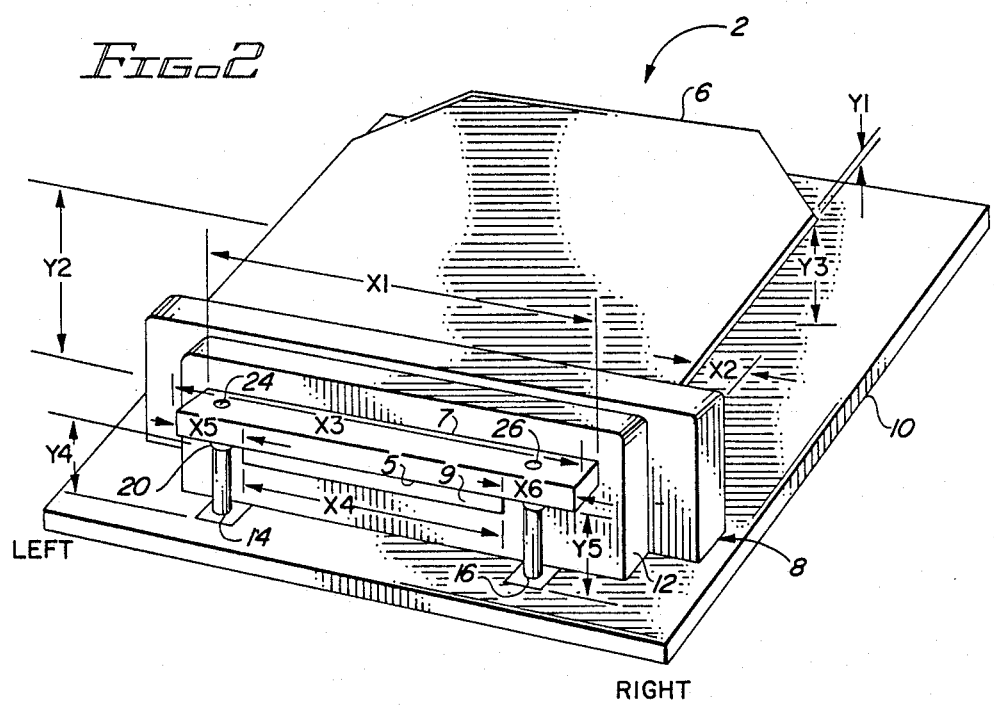
FIG. 2 is a detailed drawing of the detector assembly and collimator.

The detector assembly 2 includes the detector board 6, a high voltage plate 9, rear flange 8, a base plate 10, a xenon gas housing 12, a collimator 4, a first standoff 14, and a second standoff 16 (shown on FIG. 2). The detector board includes a linear array of detector elements 11 across the face of the board positioned parallel to a collimator slot 5. The voltage plate 9 is positioned below the substrate and parallel to detector elements 11 and spaced apart by a distance of 35 mils. The detector board 6, and voltage plate 9 are positioned into chamber 13. The board 6 and plate 9 are epoxied into chamber 13. The base plate 10 supports the assembly of detector board 6, standoffs 14 and 16, voltage plate 9, rear flange 8, and housing 12. The collimator 4 includes a top piece 7 and a bottom piece 3. The top piece 7 and bottom piece 3 are comprised of two bars of a sintered mixture of iron and tungsten (an X-ray absorbing material) with tungsten predominating to a high percentage and defining a slit 5 between parallel faces of top piece 7 and bottom piece 3. The slit is 11.5 mils in height. The collimator is secured to standoffs 14 and 16 by bolts 24 and 26 (FIG. 2). The xenon gas housing 12 contains xenon gas that is ionized when X-rays pass through the housing 12. The ionization products of the X-ray-xenon interacting strike the detector elements on the detector board 6 generating a current which is fed to appropriate recording and computation equipment. A suitable detector for measuring the X-ray intensity is disclosed in U.S. patent application Ser. No. 565,691, filed Dec. 27, 1983, titled Ionization Detector and assigned to General Electric Company, the disclosure of which is hereby incorporated by reference.

Referring to FIG. 2, X1 is the width of the piece of the detector board 6 inside the housing. X2 is the distance from the right edge of the detector board 6 to the right edge of the rear flange 8. The top collimator piece 7 width is X3. The bottom collimator piece 3 width is X4. The depth from the left edge of the top collimator piece 7 to the left edge of the bottom collimator piece 3 is X5. X6 is the depth from the right edge of the top collimator piece 7 to the right edge of the bottom collimator piece 3.

The thickness of the detector board is Y1. The height above the base plate for the left edge of the detector board 6 is Y2. The height above the base plate for the right edge of the detector board 6 is Y3. The vertical height of standoff 14 is Y4 and the vertical of standoff 16 is Y5. A shim 20 adjusts the vertical height of standoff 14 and a shim 22 adjusts the vertical height of standoff 16.

Referring now to FIG. 3, there is shown a flow chart for computing the horizontal position of the collimator. In block 100, the width of detector board 6 is determined by making repeated measurements and entering an averaged value. The edge-to-center distance for detector board 6 is determined by dividing the width by two, block 102. The procedure then continues at block 104, in which the distance from the right edge of the detector board 6 to the right edge of the rear flange 8 is measured. Repeated measurements of X2 are made and an average value is computed. The value B which is physically half of the width of detector board 6, and the average value of X2 are added for computing a centerline for the detector board with respect to the right edge of rear flange 6, block 106. The centerline for the detector board 6 is then marked on the housing 12, block 108.

In block 110, repeated measurements of the width of the top collimator piece 7 are made and an average value is determined. The center distance for the top collimator piece 7 is computed in block 112. C, the center, equals X3/2. In block 114 an average width of the bottom collimator piece 3 is determined. An average depth X5 is then determined, block 116. An average depth X6 is determined, block 118. A difference D between X5 and X6 is computed in block 120. D is then tested, block 122. If D is positive, then the centerline of the collimator is equal to C−D, block 124. If D is negative, then the centerline of the collimator is C+D, block 126. The horizontal centerline of the collimator is then marked on the top collimator piece 7, block 128. To align the horizontal centerline of the collimator and the center detector, the two centerlines are matched, block 130.

FIG. 4 is a flow diagram describing the method of aligning the detector board 6 and collimator 4 in the vertical direction. In block 200, an average value Y1 for the detector board 6 thickness is determined. An average height Y2 of the top of board 6 above the base plate 10 on the left side of the detector board 6 edge is determined, block 202. A average height Y3 of the top of board 6 above the base plate 8 for the right side of the detector board 6 is determined, block 204. The left vertical height of detector board 6 is found by subtracting Y1 from Y2. Subtracting 17.5 mils from this value, block 206, to obtain the right vertical center between plate 9 and elements 11. 17.5 mils corresponds to the one half thickness of the separation between plate 9 and detector elements 11. The right side vertical height of the detector board is computed by subtracting Y1 from Y3 and then subtracting 17.5 mils from this value, block 208, to obtain the right vertical center between plate 9 and elements 11.

Standoff 14 and standoff 16 are installed on base plate 10 with threaded members in the bottom of base plate 10. An average height for standoff 14 and for standoff 16 is determined separately. The average height of standoff 14 is Y4 and the average height of standoff 16 is Y5, block 210. One half the distance of slit 5 (5.75 mils) is substracted from Y4 and Y5, block 212. This value is the vertical distance to the center of slit 5. The thickness for the left shim 20 is computed by subtracting Y4 from Y2, block 214. The right shim thickness is computed by subtracting Y5 from Y3, block 216. The collimator is then assembled onto the base plate 10 by placing shim 20 with the computed thickness between the collimator and standoff 14 and shim 22 between collimator and standoff 16. Threaded members 24 and 26 holds the collimator on standoffs 14 and 16.

The collimator is assembled to the detector with the appropriate shim thicknesses between the collimator and standoffs. The centerline in the horizontal direction for the collimator is aligned to the detector's centerline. The assembly is then secured by tightening the threaded members 24 and 26, block 217.

What has been shown is a method for assembling and aligning a collimator in front of a linear array detector board. The method aligns the collimator with the linear detector board in the horizontal and vertical directions.

It is to be understood that the above described embodiment of the invention is illustrative only, and that modifications thereof may occur to those skilCled in the art. Accordingly, this invention is not to be regarded as limited to the embodiment disclosed herein, but is to be limited only as defined by the appended claims.

What is claimed is:

1. A method for aligning a X-ray beam collimator to a linear array X-ray detector board having a linear array of detector elements across the face of the board, the board being positioned inside a housing:
    (a) obtaining a plurality of measurements of the width of said linear array;
    (b) determining an average value representative of said width;
    (c) obtaining a plurality of measurements between a first predetermined point on said housing and a second predetermined point on said board;
    (d) determining an average value of the measurements of step (c);
    (e) determining a horizontal centerline for said detector from the average values obtained from steps (b) and (d);
    (f) locating a horizontal centerline of said collimator; and
    (g) attaching said collimator to said housing such that said horizontal centerline of said collimator aligns with said horizontal centerline of said detector.

2. The method of claim 1, wherein the board is oriented in a plane parallel to the plane of the baseplate further comprising the steps of:
    (a) obtaining a plurality of measurements for the perpendicular distance between the detector board and the baseplate;
    (b) determining an average value representative of said perpendicular distance; and (c) adjusting the position of the collimator in said perpendicular direction such that a vertical is aligned with the plane of the detector board.

3. The method of claim 1 wherein the board comprises a substantially rectangular planar member having the linear array of detector elements on a first surface, the housing including a baseplate oriented in a plane parallel to the first surface of the board and a high-voltage plate positioned between the first surface and the baseplate a predetermined distance from the first surface, the method comprising the further steps of:

(h) obtaining a plurality of measurements of the thickness of the board and the perpendicular distance from a surface of the board distal of the baseplate to the baseplate;

(i) computing an average value of each of the measured quantities of step (h);

(j) subtracting the average thickness of the board from the average perpendicular distance for obtaining a distance from the detector elements to the baseplate;

(k) subtracting half the predetermined distance between the board and high voltage plate from the average distance of step (j) for locating a vertical center between the board and high voltage plate; and (l) adjusting the collimator vertically such that its vertical center is aligned with the vertical center located in step (k).

* * * * *

UNITED STATES PATENT AND TRADEMARK OFFICE
CERTIFICATE OF CORRECTION

PATENT NO. :   4,734,988

DATED      :   April 5, 1988

INVENTOR(S) :  Douglas S. Steele, Casmir R. Trzaskos

It is certified that error appears in the above-identified patent and that said Letters Patent is hereby corrected as shown below:

On the title page

(75) INVENTORSHIP:  After Casmir R. Trzaskos, add
                         --Theodore W. Sippel, Cincinnati, Ohio--.

Signed and Sealed this

Fourteenth Day of February, 1989

*Attest:*

DONALD J. QUIGG

*Attesting Officer*   *Commissioner of Patents and Trademarks*